United States Patent
Albadawi et al.

(10) Patent No.: US 9,903,755 B2
(45) Date of Patent: Feb. 27, 2018

(54) INDOORS / OUTDOORS DETECTION

(71) Applicant: Microsoft Technology Licensing, LLC, Redmond, WA (US)

(72) Inventors: Haithem Albadawi, Redmond, WA (US); Han Yee Mimi Fung, Bellevue, WA (US); Farah Shariff, Kirkland, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 14/875,483

(22) Filed: Oct. 5, 2015

(65) Prior Publication Data
US 2017/0097258 A1  Apr. 6, 2017

(51) Int. Cl.
*G08B 21/00* (2006.01)
*G01J 1/42* (2006.01)
*A61B 5/11* (2006.01)
*G08B 21/18* (2006.01)
(Continued)

(52) U.S. Cl.
CPC .......... *G01J 1/429* (2013.01); *A61B 5/1112* (2013.01); *G01C 21/00* (2013.01); *G01J 1/4204* (2013.01); *G06F 19/3481* (2013.01); *G08B 21/182* (2013.01); *G01J 2001/4266* (2013.01)

(58) Field of Classification Search
CPC .. G01J 1/429; G01J 1/4204; G01J 2001/4266; A61B 5/1112; G08B 21/182
See application file for complete search history.

(56) References Cited

U.S. PATENT DOCUMENTS 4,962,910 A * 10/1990 Shimizu .................. G01J 1/429
                                                         250/372
5,148,023 A *  9/1992 Hayashi .................. G01J 1/429
                                                         250/372
(Continued)

FOREIGN PATENT DOCUMENTS

WO    2015028462 A1    3/2015
WO    2015065516 A1    5/2015

OTHER PUBLICATIONS

Zhou, et al., "IODetector: A Generic Service for Indoor Outdoor Detection", In Proceedings of the 10th ACM Conference on Embedded Network Sensor Systems, Nov. 6, 2012, pp. 133-126.
(Continued)

*Primary Examiner* — Jeffery Hofsass
(74) *Attorney, Agent, or Firm* — Workman Nydegger

(57) ABSTRACT

Determining time spent outdoors. A method includes, at a first time, using one or more primary criteria including one or more criteria related to information provided by a first hardware input sensor on a device, to determine that the device is outdoors. The method further includes at one or more other times, using one or more secondary criteria, different than the primary criteria, the secondary criteria related to information provided by one or more second hardware input sensors, to determine continuity of the device being outdoors from the first time to the one or more other times. The method further includes based on determining that the device is outdoors and determining continuity of the device being outdoors from the first time to the one or more other times, identifying a total amount of time that the device has been outdoors.

20 Claims, 6 Drawing Sheets

(51) Int. Cl.
*G01C 21/00* (2006.01)
*G06F 19/00* (2018.01)

(56) References Cited

U.S. PATENT DOCUMENTS

| | | | | |
|---|---|---|---|---|
| 6,060,321 | A * | 5/2000 | Hovorka | G01N 31/22 |
| | | | | 422/421 |
| 9,068,887 | B1 | 6/2015 | Bennouri et al. | |
| 2003/0150998 | A1 * | 8/2003 | Shin | G01J 1/429 |
| | | | | 250/372 |
| 2006/0230108 | A1 | 10/2006 | Tatsuta et al. | |
| 2006/0289779 | A1 | 12/2006 | Marmaropoulos | |
| 2009/0043504 | A1 * | 2/2009 | Bandyopadhyay | G01C 17/38 |
| | | | | 701/469 |
| 2009/0180356 | A1 * | 7/2009 | Fujisawa | G01S 19/14 |
| | | | | 368/47 |
| 2011/0024307 | A1 * | 2/2011 | Simpson | A61B 5/14532 |
| | | | | 205/782 |
| 2012/0056745 | A1 * | 3/2012 | Noguchi | G08B 21/24 |
| | | | | 340/573.1 |
| 2012/0326046 | A1 * | 12/2012 | Aslam | G01J 1/0233 |
| | | | | 250/372 |
| 2014/0107493 | A1 * | 4/2014 | Yuen | H04W 4/027 |
| | | | | 600/473 |
| 2014/0129560 | A1 | 5/2014 | Grokop et al. | |
| 2014/0171068 | A1 * | 6/2014 | Marti | G01S 1/047 |
| | | | | 455/427 |
| 2014/0279790 | A1 | 9/2014 | Ramachandran et al. | |
| 2014/0374600 | A1 | 12/2014 | Gokingco et al. | |
| 2015/0097731 | A1 | 4/2015 | Russell | |
| 2015/0102208 | A1 * | 4/2015 | Appelboom | G01J 1/4204 |
| | | | | 250/208.2 |
| 2016/0061657 | A1 * | 3/2016 | Lapiere | G01J 1/429 |
| | | | | 250/372 |
| 2017/0118854 | A1 * | 4/2017 | Dumont | H05K 5/0247 |

OTHER PUBLICATIONS

Zhang, et al., "See UV on Your Skin: An Ultraviolet Sensing and Visualization System", In Proceedings of the 8th International Conference on Body Area Networks, Sep. 30, 2013, pp. 22-28.
Griffiths, Sarah, "The Bracelet That Prevents Sunburn: $100 Gadget Tells You When to Slap on Sunscreen and Warns When You've Been out Too Long", Published on: Jan. 10, 2014 Available at: http://www.dailymail.co.uk/sciencetech/article-2537168/The-bracelet-stops-SUNBURN-100-gadget-tells-slap-sunscreen-warns-youve-long.html.
"Adding UV Sensing to Wearables & Consumer Applications", In White paper of Silicon Labs, Aug. 11, 2015, pp. 1-7.
Frank, Michael, "The Microsoft Band Is the Wearable Nobody's Talking About", Published on: Apr. 13, 2015. Available at: http://www.outsideonline.com/1965931/microsoft%E2%80%99s-band-wearable-nobody%E2%80%99s-talking-about.
"SparkFun UV Sensor Breakout—ML8511", Published on: Mar. 30, 2015 Available at: https://www.sparkfun.com/products/12705.
"Barclays: Apple's 'iWatch' could Include UV Light Exposure Sensor", Published on: Apr. 7, 2014 Available at: http://appleinsider.com/articles/14/04/07/barclays-apples-iwatch-could-include-uv-light-exposure-sensor.
International Search Report and Written Opinion issued in PCT Application No. PCT/US2016/053856 dated Dec. 1, 2016.
International Preliminary Report on Patentability issued in PCT Patent Application No. PCT/US2016/053856 dated Jul. 19, 2017.
2nd Written Opinion issued in PCT Application No. PCT/US2016/053856 dated Apr. 20, 2017.

* cited by examiner

INDOORS / OUTDOORS DETECTION

BACKGROUND

Background and Relevant Art

Exposure to sunlight can have both positive and negative effects. In particular, exposure to UV-B rays can help the human body produce Vitamin D, which provides a number of healthful benefits. However, exposure to UV-A rays can cause skin aging and too much exposure to UV-B rays can cause skin cancer. Thus, it is useful to know the amount of time spent in outdoor environments to be able to approximate how much exposure to various UV rays has occurred. Currently, there is no easy way to track the amount of exposure to outdoor environments.

For example, one previous solution included UV indicator stickers and wristbands. An individual might wear a sticker or wristband, when outdoors and reapply sunblock when the sticker or wristband changes color to indicate the need, to reapply. In this scenario, the user has to monitor the sticker or wristband color-change. Additionally, the sticker or wristband may fall off unnoticed if the user exercises vigorously.

Another previous solution includes hand-held UV meters. However, this solution requires manual captures for each UV index reading, with one reading per capture. The user has to remember to manually capture UV readings throughout the day if they would like to monitor their UV exposure.

UV reminder apps on cell phones usually rely on a UV index reported from a meteorological station. However, there is usually a lag in the reporting, and the condition at the station may differ from the user's location.

Each of these solutions rely on the user to remember to actively monitor themselves outdoors, including manually monitoring how long the user has been outdoors.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

One embodiment illustrated herein includes a method that may be practiced in a computing environment. The method includes acts for determining time spent outdoors. The method includes, at a first time, using one or more primary criteria including criteria related to information provided by a first hardware input sensor on a device, to determine that the device is outdoors as a result of the primary criteria being met. The method further includes at one or more other times, using one or more secondary criteria, different than the primary criteria, the secondary criteria related to information provided by one or more second hardware input sensors, to determine continuity of the device being outdoors from the first time to the one or more other times as a result of one or more of the one or more secondary criteria being met. The method further includes based on determining that the device is outdoors and determining continuity of the device being outdoors from the first time to the one or more other times, identifying a total amount of time that the device has been outdoors.

Another embodiment illustrated herein includes a method that may be practiced in a computing environment. The method includes acts for determining time spent exposed to UV radiation. The method includes, at a first time, using primary criteria including criteria related to information provided by a first hardware input sensor on a device, to determine that the device is exposed to UV radiation as a result of the primary criteria being met. The method further includes at one or more other times, using one or more secondary criteria, different than the primary criteria, the secondary criteria related to information provided by one or more second hardware input sensors, to determine continuity of the device being exposed to UV radiation from the first time to the one or more other times as a result of one or more of the one or more secondary criteria being met. The method further includes based on determining that the device is exposed to UV radiation and determining continuity of the device being exposed to UV radiation from the first time to the one or more other times, identifying a total amount of time that the device has been exposed to UV radiation.

Another embodiment includes a device configured to detect time spent outdoors. The device includes one or more first hardware sensors. The one or more first hardware sensors are configured to detect one or more first factors that can be used to determine that a device is outdoors. The device includes one or more second hardware sensors. The one or more second hardware sensors are configured to detect one or more second factors that can be used to determine that a device is outdoors. The device includes one or more processors. The one or more processors are configured to, at a first time, use primary criteria including criteria related to information provided by the one or more first hardware input sensors, to determine that the device is outdoors as a result of the primary criteria being met. The one or more processors are further configured to at one or more other times, use one or more secondary criteria, different than the primary criteria, the secondary criteria are related to information provided by the one or more second hardware input sensors, to determine continuity of the device being outdoors from the first time to the one or more other times as a result of one or more of the one or more secondary criteria being met. The one or more processors are further configured to, based on determining that the device is outdoors and determining continuity of the device being outdoors from the first time to the one or more other times, identify a total amount of time that the device has been outdoors.

Another embodiment includes a device configured to detect time spent exposed to UV radiation. The d vice includes a UV sensor, wherein the UV sensor is configured to detect UV radiation. The device further includes one or more second hardware sensors, wherein the one or more second hardware sensors are configured to detect one or more second factors other than UV radiation that indicate that a device is outdoors, and therefore potentially exposed to UV radiation. The device further includes one or more processors. The one or more processors are configured to, at a first time, use primary criteria including criteria related to UV radiation thresholds to determine that the device is exposed to UV radiation as a result of the primary criteria being met. The one or more processors are further configured to, at one or more other times, using one or more secondary criteria, different than the primary criteria, the secondary criteria related to informal on provided by the one or more second hardware input sensors, to determine continuity of the device being exposed to UV radiation from the first time to the one or ore other times as a result of one or more of the one or more secondary criteria being met. The one or more processors are configured to, based on determining that the device is exposed to UV radiation and determining continuity of the device being exposed to UV radiation from the first time to the one or more other times, identify a total amount of time that the device has been outdoors.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION

Figure 1:
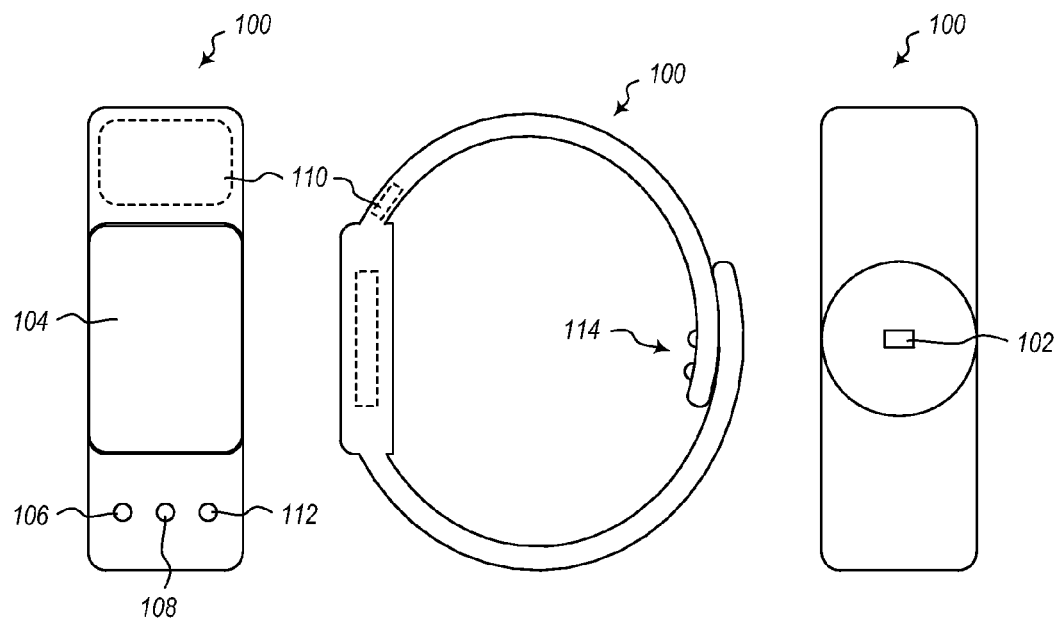
FIG. 1 illustrates a fitness wearable device that is configured to detect if a device is outdoors or exposed to UV radiation.

Embodiments herein may include a device which automatically and repeatedly, over time (e.g., periodically), performs actions to determine if the device is indoors or outdoors (or alternatively if the device is in the presence of UV radiation or not). For example, such a device may be a wearable device, such as a fitness tracker, watch, jewelry, or other device. Based on repeatedly, over time, determining if the device is indoors or outdoors (or in the presence of UV radiation or not), the device can estimate amounts of time spent indoors or outdoors (or in the presence of UV radiation or not), whether healthful or harmful. The device can then provide output to a user based on the estimations. Such output may take a number of different forms, such as raw data output indicating an estimated amount of time for exposure to various conditions or energy sources. Alternatively or additionally, such output may include tailored recommendations to the user. For example, the output may encourage the user to remain outdoors or go indoors. Alternatively or additionally the output may encourage the user to go outdoors to obtain certain healthful benefits.

There are various challenges when attempting to detect that a device is outdoors. For example, the device may have a UV sensor that is able to detect UV radiation which indicates a high likelihood that the device is outdoors. However, after initially detecting UV radiation in sufficiently high amounts to indicate that the device is outdoors, the device may be repositioned such that it is no longer able to detect UV radiation in sufficiently high amounts to indicate that the device is outdoors. However, in some embodiments, the device may be able to detect ambient light in sufficiently high amounts using a different sensor, such as an ambient light sensor, that while not detecting any UV radiation, nonetheless can be used as an indicator that the device continues to be outdoors, especially in view of a temporally proximal reading from the UV sensor indicating that the device is outdoors.

Thus, in general, devices may evaluate factors to determine if one or more primary criteria are met to determine that the device is outdoors or in the presence of a threshold amount of UV radiation. Factors can be used to indicate that a device is outdoors, and therefore potentially exposed to UV radiation. In particular, factors, as used herein, refer to various inputs and/or operands that can be evaluated to determine if the factors are of magnitudes or values, alone or in combination, that indicate that certain criteria are met indicating that a device is outdoors. In some embodiments, when the primary criteria are no longer met, the device may evaluate factors to determine that one or more secondary criteria are met to determine that the device likely remains outdoors even though the primary criteria are no longer met.

In the examples above, a sufficient amount of UV radiation being detected by a UV sensor may satisfy the primary criteria while a sufficient amount of ambient light may satisfy the secondary criteria. However, other means may be used to meet criteria. For example, activating the primary criteria could include a user indicating in a user interface that they are outdoors. The secondary criteria could include evaluation of factors related to threshold GPS signal strength, barometer readings, or other information.

Referring now to FIG. 1, an example device 100 is illustrated. In this example, the device 100 is a wearable device, and in particular a fitness tracker. The device 100, in the illustrated example, includes a UV sensor 102. The UV sensor 102 can be used, along with other related circuitry, to measure factor, which in this case, an amount of UV radiation which can be correlated to identify a UV index in the area where the measurement is being taken. If a UV radiation reading is sufficiently high (i.e., meets the primary criteria), a determination can be made that the device 100 is outdoors.

In some embodiments, the UV sensor 102 and related circuitry can be activated for taking a UV reading manually by a user. For example, the device 100 includes a touchscreen 104. The touchscreen can display a user interface that allows the user to select an option that causes the UV sensor 102 and related circuitry to measure UV radiation. In this scenario, typically the user will point the UV sensor 102 towards the Sun when activating the UV sensor 102 and related circuitry, such that an accurate (and potentially maximum) UV radiation reading can be obtained. As noted, if there is sufficient UV radiation being detected (e.g., in one example, a UV index greater than or equal to 2), a determination is made by the device 100 that the device is outdoors. Thus, primary criteria, in this example namely a UV radiation reading meeting a predetermined threshold, is met. As a result the device determines that it is outdoors (or in the presence of UV radiation).

In other embodiments, the UV sensor 102 and related circuitry can be activated as a background operation for automatically taking a UV reading. For example a periodic background operation may be performed to activate the UV sensor 102 and related circuitry to obtain a UV radiation reading. In one example embodiment, a sample may be taken using the UV sensor 102 every one minute (or some other defined interval). In one particular example, the UV sensor 102 is sampled every 5 seconds in each one minute interval, and the peak measurement from each one minute interval is used as the one minute sample. During one of these one minute samples, a sufficiently high UV radiation reading may be measured to meet the primary criteria.

Figure 2:
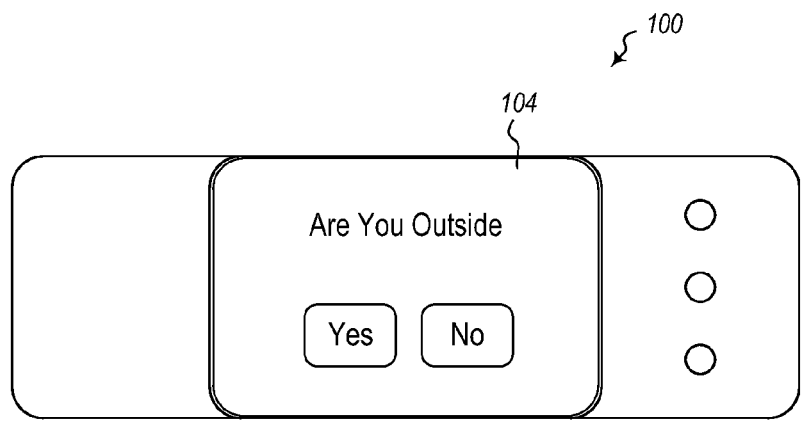
FIG. 2 illustrates a touchscreen display of the device

Note that other criteria may be defined as the primary criteria that when met, indicate that the device 100 is outdoors (or in the presence of UV of radiation). For example, FIG. 2 illustrates that the device 100 displays on the touchscreen an interface that allows a user to manually indicate whether or not the device 100 is outdoors or not. Thus, in this example, the primary criteria may be met by a user selecting an option in a user interface manually indicating that the device is outdoors. The hardware sensor in this case might include user interface sensors, such as buttons, touchscreens, pointing devices, and the like.

Secondary criteria being met may be used to determine that the device remains outdoors. Secondary criteria will be illustrated in more detail below.

In some embodiments, the secondary criteria may be used when the primary criteria are no longer met. Thus, for example, in the examples illustrated above, UV radiation readings may no longer meet the threshold criteria needed to meet the primary criteria indicating that the device is outdoors. In some such embodiments, before reverting to the secondary criteria, the primary criteria must need to not be met according to some predetermined condition. For example, the predetermined condition may specify that UV radiation must be measured below the threshold of the primary criteria for at least 5 samples before secondary criteria are used to determine whether or not the device 100 remains outdoors.

In the case where user input is used, there will often be only a single event that meets the primary criteria (i.e., the user selecting a user interface element indicating that the device 100 is outdoors) such that once the primary criteria are met, the secondary criteria are the next criteria used to determine whether or not the device 100 remains outdoors. In some examples, secondary factors may be sampled at a given sample rate to determine if the secondary criteria are met.

Various different criteria may be used additionally or alternatively as part of the secondary criteria to determine if the device remains outdoors. In the example illustrated in FIG. 1, the device 100 includes an ambient light sensor (ALS) 106, a barometer 108, a GPS sensor 110, and a microphone 112. Each of these devices (and other devices though not enumerated here) could be used (singly and/or in combination) to collect secondary data to determine if the device 100 remains outdoors after the primary criteria are met.

For example, the secondary criteria may specify a certain threshold of ambient light. Thus, the ALS 106 could be used to measure ambient lighting for the environment in which the device 100 is operating to determine if the ambient lighting meets the threshold.

Figure 3:
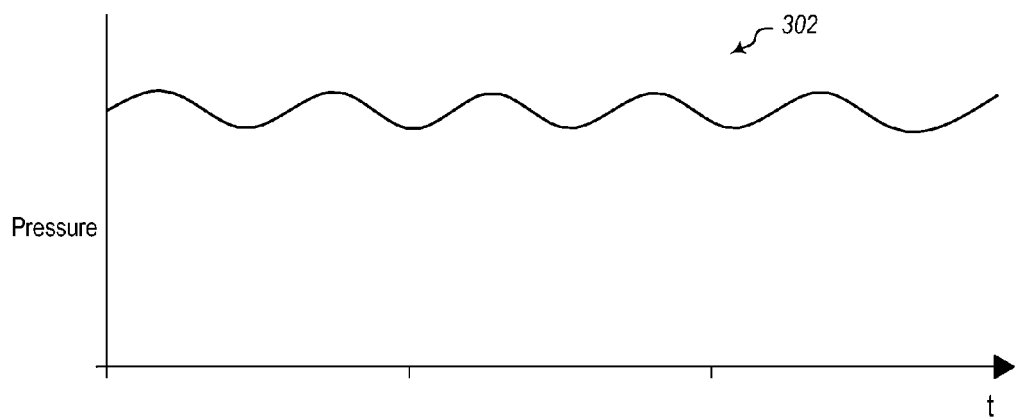
FIG. 3 illustrates a graph of barometric pressure in an indoor environment and a graph of barometric pressure in an outdoor environment.
Figure 3:
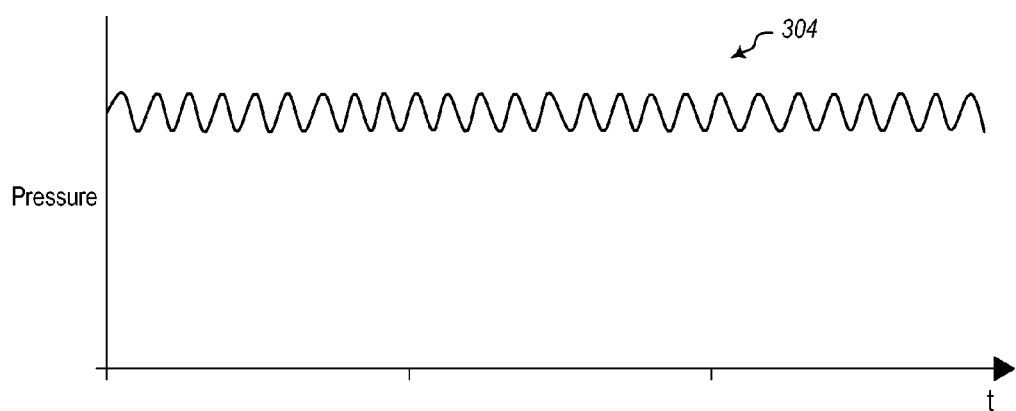

The secondary criteria may additionally or alternatively specify certain barometric pressure profile conditions. In particular, barometric pressure profiles when the device 100 is indoors are different than barometric pressure profiles when the device is outdoors. In particular, when the device 100 is outdoors, a barometric pressure profile measured by the barometer 108 will have more noise in the signal than a barometric pressure profile measured by the barometer 108 when the device 100 is indoors. For example, reference is made to FIG. 3. FIG. 3 illustrates a graph 302 of barometric pressure when the device 100 is indoors and a graph 304 of barometric pressure when the device is outdoors. The graphs show barometric pressure over time. However, the graphs illustrate that a signal measured by the barometer 108 when the device is outdoors has a lower signal to noise ratio than a signal measured by the barometer when the device is indoors. Thus, the secondary criteria could include a barometric pressure profile which may include a threshold signal to noise ratio.

The secondary criteria may additionally or alternatively specify certain GPS sensor characteristics. In particular, GPS signals are typically stronger outdoors than indoors. Thus, embodiments can measure a GPS signal strength at the GPS sensor 110. The secondary criteria may specify a certain GPS signal strength threshold.

The secondary criteria may additionally or alternatively specify certain sound pressure profile conditions. In particular, sound pressures are often lower outdoors than indoors because sound is dissipated more easily outdoors than indoors. Thus, the microphone 112 could be used to measure sound pressure. The secondary criteria may specify a sound pressure threshold, below which, it can be estimated that device is outdoors.

Various other criteria may be evaluated alternatively or additionally as part of the secondary criteria although not enumerated here. Further, it should be appreciated that various factors may be used in combination as part of the secondary criteria.

Further still, it should be appreciated that in some embodiments, when using measurements of different sensors, each measurement may be used to create a confidence value indicating of confidence level of whether or not the device is indoors or outdoors. For example, ambient light measured at one level may result in an 80% confidence that the device is outdoors, A lower ambient light level may result in a 50% confidence level that the device is outdoors. Further different confidence levels resulting from different measurements may be used to create a composite confidence level. Thus for example, a confidence level of 80% determined from an ambient light level combined with an 80% confidence level determined from a GPS signal may result in an overall 90% confidence level.

Note that when determining overall confidence levels (or even when computing confidence levels individually), the different confidence levels may be weighted or selectively adjusted. For example, knowing time of day may be used when determining how much weight (or even the confidence level in the first instance) is given to an ambient light reading. Similarly, if the device 100 is able to access current weather conditions, this could be factored in to sensor readings. Thus, for example, an ambient light threshold (or confidence level) may be raised if it is known to be sunny.

Similarly, if the device 100 is able to access location information, this information can be used to adjust thresholds and/or confidence levels. For example, consider a case where using the OPS sensor 110 it can be determined that the device 100 is proximate a football stadium. If the device is able to access information indicating that a football game is under way, then the device 100 might expect high sound levels to be detected by the microphone 112 if the device is outdoors. Thus, the secondary criteria could include such factors.

Note that in other embodiments, conditions could still exist such that the primary criteria are still met, but these other embodiments nonetheless use the secondary criteria to determine that the device remains outdoors. Thus, for example, once primary criteria are met in a single sample, active monitoring may instead switch to evaluating secondary criteria to determine if the device remains outdoors.

Embodiments may use various algorithms to determine the length of time that the device 100 has been outdoors. For example, time determination may be made based on when various criteria were met. Most simply, an algorithm may determine the difference in time from when a primary or secondary criteria was met to a different time when primary or secondary criteria was met. Typically, an instance of primary criteria being met will need to have occurred in a continuum of primary and secondary criteria being met (as will be illustrated in more detail below).

While in the examples above, the primary criteria are illustrated as being met first, it should be appreciated that in other embodiments, the primary criteria may actually be met after the secondary criteria are met. Thus, in some embodiments, the secondary criteria will be met, but the device will not be determined, to be outdoors. At a later time, the primary criteria may be met, and samples used for evaluating secondary criteria occurring prior to the primary criteria being met may be examined. If the secondary criteria was met prior to and continuously with the primary criteria being met, embodiments may determine that the device was outdoors prior to the primary criteria being met and may use occurrence of the secondary criteria being met prior to the primary criteria being met when calculating total time outdoors.

Thus, for example, time outdoors may be calculated as follows where P represents instances of primary criteria being met and S represents instances of secondary criteria being met. In a case where $P_1$ is followed by $S_1$, the time outdoors may be $S_1 - P_1$. In a case where $S_1$ is followed by $P_1$, the time outdoors may be $P_1 - S_1$. In a case where $S_1$ is followed by $P_1$, which is followed by $S_2$, the time outdoors may be $S_2 - S_1$. More generally time outdoors may be calculated as $\max(S_1$ to $S_m$ and $P_1$ to $P_n)$ minus $\min(S_1$ to $S_m$ and $P_1$ to $P_n)$ where at least one instance of P occurs and where $S_1$ to $S_m$ and $P_1$ to $P_n$ are continuous without intervening instances where P or S do not occur (or in some embodiments when more than various combinations of a predetermined number of samples where P and/or S do not occur).

However other embodiments may only calculate time using an occurrence of P and one or more subsequent occurrences of S. This may be done to allow a user to control when time begins to be measured.

Figure 4:
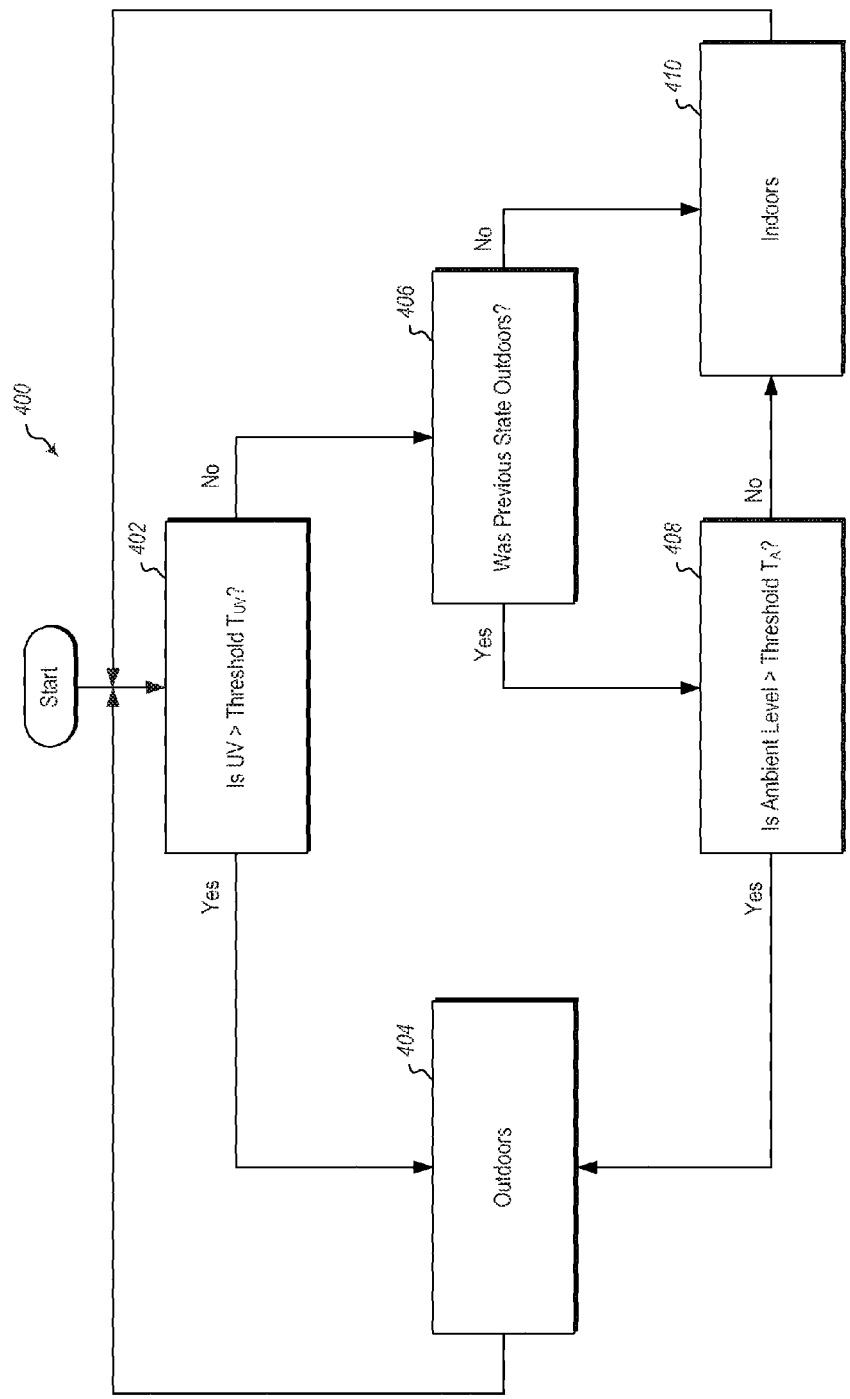
FIG. 4 illustrates a flow illustrating how a UV sensor and ALS sensor can be used for detecting if a device is indoors or outdoors.

With reference now to FIG. 4, the following illustrates an example scenario. As illustrated at 402, of the flow 400, embodiments use the UV sensor 102 to trigger an indication of the device being outdoors as illustrated at 404. This is done by the UV sensor reading a UV index over the threshold T(UV)).

If after a previous state of being outdoors as illustrated at 406, the next UV reading obtained is zero, then as illustrated at 408 the ambient light sensor 106 is used to determine if the user is still outdoors.

If the ambient light sensor indicates that the user is exposed to ambient light that is greater than the threshold T(ALS), the user is still outdoors as illustrated at 404. If not, then the user is not outdoors anymore as illustrated at 410.

Note that in the illustrated example in FIG. 1, the device 100 includes the UV sensor 102 on one face of the device 100 and the ambient light sensor 106 on an opposite face of the device 100. Thus, if one of the sensors is shielded from outdoor light exposure, it is likely that the other sensor will be directed towards the outdoor light exposure. Thus, embodiments may position sensors on the device 100 in ways that provide multi directional sensing with different devices sensing different inputs in different directions.

With the ability to classify indoor/outdoor exposure states, embodiments can provide other useful metrics, such as total exposure minutes over a given time, total consecutive exposure minutes, and the UV and ambient light levels users to exposed to over time, and send active reminders to users to, for instance, apply sunblock after a certain time has elapsed, or to get exposure to brighter settings. Thus, embodiments may have the ability to provide active reminders to users such that users do not have to remember to check instruments that monitor outdoor metrics.

Figure 5A:
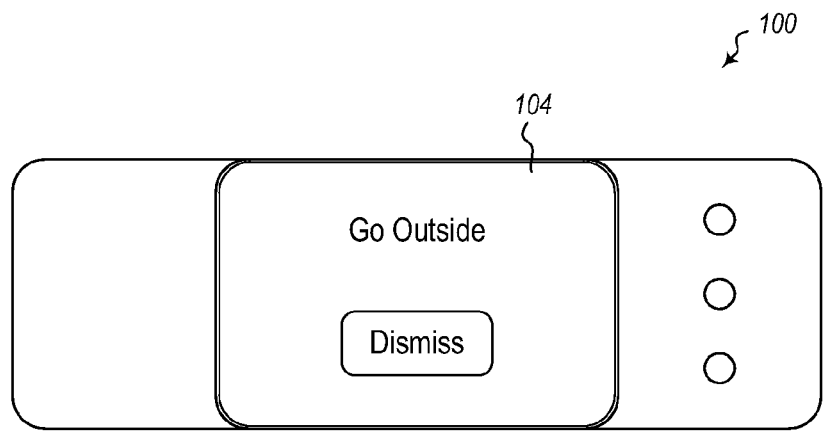
FIG. 5A illustrates a message displayed on a device to a user.
Figure 5B:
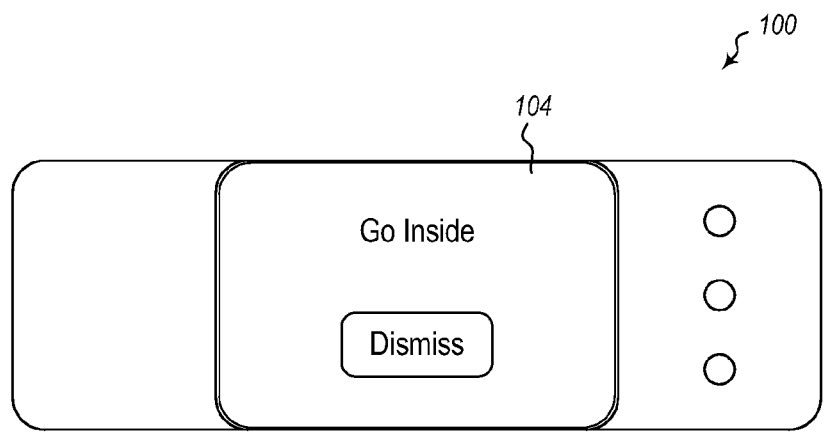
FIG. 5B illustrates a message displayed on a device to a user.
Figure 5C:
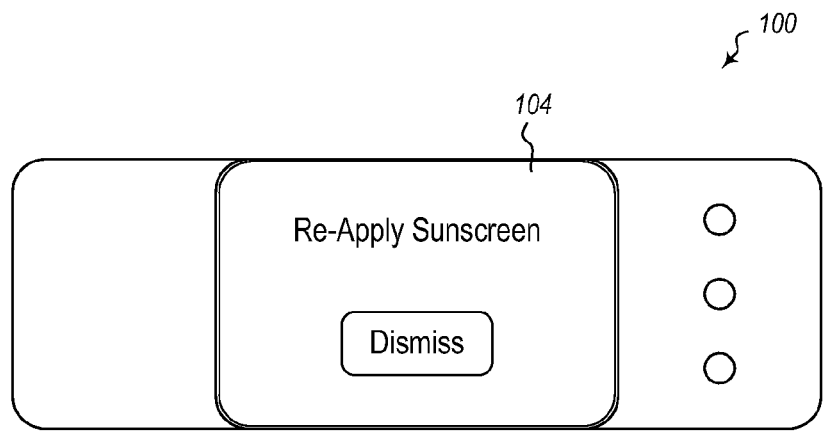
FIG. 5C illustrates a message displayed on a device to a user.

FIGS. 5A, 5B and 5C illustrate examples of this functionality. In particular, FIG. 5A illustrates the device 100 displaying on the touchscreen an indication to a user that they should go outdoors to obtain sunlight exposure. FIG. 5B illustrates the device 100 displaying on the touchscreen 104 an indication to a user that they should go inside to limit sunlight exposure. FIG. 5C illustrates the device 100 displaying on the touchscreen 104 an indication to a user that they should re-apply sunscreen. This message (or others) may be displayed as a result of determinations about how much exposure to UV radiation or outdoor environments the device 100 has experienced.

In some embodiments, timing for when indicators are displayed to a user may be selectable and/or otherwise variable. For example, a user may specify using a user interface when they want to be notified. For example, the user may specify, such as by interacting with a user interface implemented by the touchscreen 104 that they wish to be notified after two hours of outdoor exposure.

Alternatively or additionally, the device 100 may include additional functionality that allows the device to detect certain conditions and adjust the amount of time before a notification is provided to a user.

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 6:
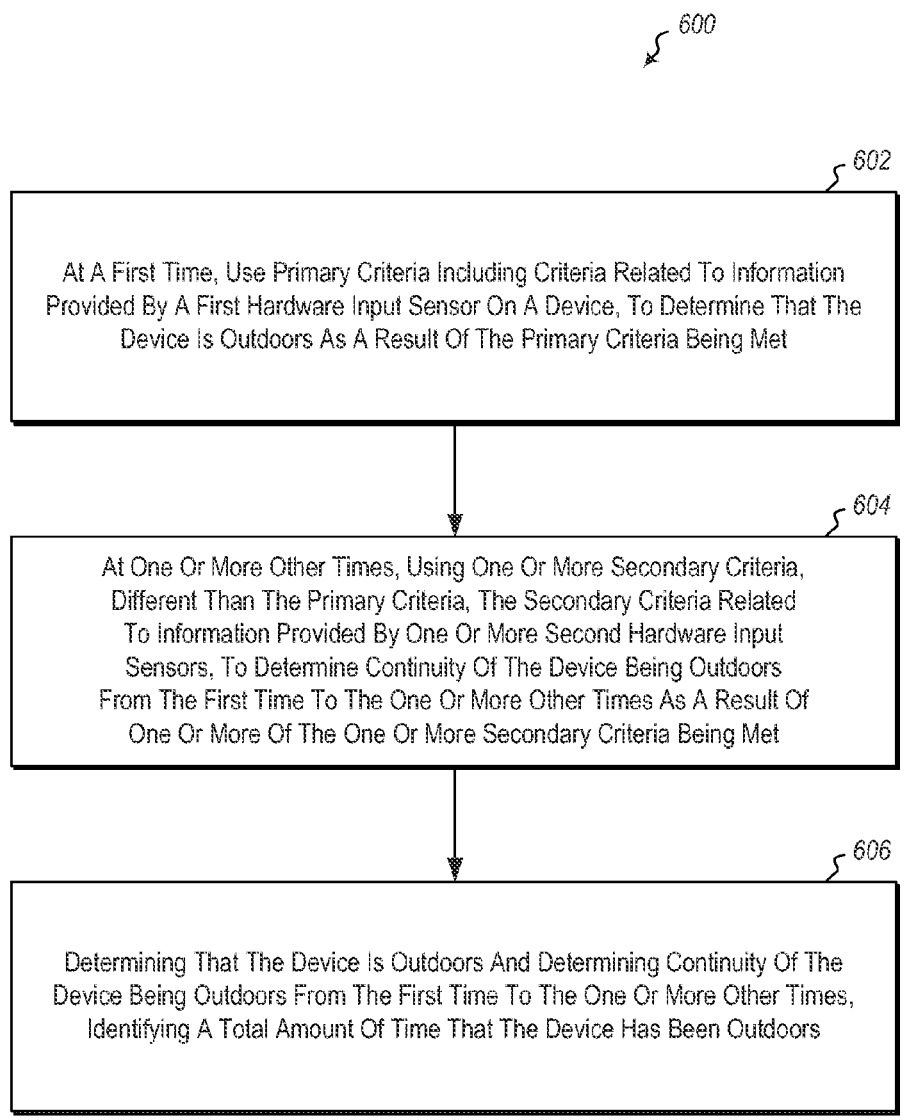
FIG. 6 illustrates a method of determining time spent outdoors.

Referring now to FIG. 6, a method 600 is illustrated. The method 600 may be practiced in a computing environment and includes acts for determining time spent outdoors. The method includes at a first time, using primary criteria including criteria related to information provided by a first hardware input sensor on a device, to determine that the device is outdoors as a result of the primary criteria being met (act 602). Thus for example, embodiments may have criteria related to UV exposure thresholds. UV exposure may be detected by the UV sensor 102 illustrated in FIG. 1.

The method 600 further includes, at one or more other times (which could be either subsequent or prior times), using one or more secondary criteria, different than the primary criteria, the secondary criteria related to information provided by one or more second hardware input sensors, to determine continuity of the device being outdoors from the first time to the one or more other times as a result of one or more of the one or more secondary criteria being met (act 604). Thus, for example, secondary criteria may be related to ambient light, barometric pressure, GPS signals, sound pressure, etc. Other appropriate sensors may be used to detect whether or not these criteria are met. Embodiments can determine that the primary criteria are continuous with the secondary criteria. Thus, in one example, the primary criteria may be met, followed by (or in some embodiments preceded by) the secondary criteria being met without intervening samples (or in some embodiments less than some predetermined number of samples) where the secondary criteria are not met. Often the primary criteria may be met and the may no longer be met, but the secondary criteria being met may be an indicator that the device remains outdoors.

The method further includes, based on determining that the device is outdoors and determining continuity of the device being outdoors from the first time to the one or more other times, identifying a total amount of time that the device has been outdoors (act 606). Thus, for example, as illustrated above, amount of times outdoors can be calculated by subtracting a first time from a most recent time.

The method 600 may further include determining that the primary criteria are no longer met, and be practiced where using one or more secondary criteria, different than the primary criteria are performed as a result of determining that the primary criteria are no longer met. Thus, for example, time outdoors may be calculated using the primary criteria so long as it is met, but when it is no longer met, embodiments can then evaluate the secondary criteria to see if it is met so as to be able to make a determination that the device is still outdoors. In some such embodiments, determining that the primary criteria are no longer met comprises determining that the primary criteria are no longer met over a plurality of samples of information provided by the first hardware input sensor. Thus for example, in some embodiments, the secondary criteria are not evaluated until and unless the primary criteria have not been met for more than some predetermined number of samples from the first hardware input sensors.

The method 600 may be practiced where the one or more secondary criteria are not reliable for indicating that the device is outdoors outside of the context of the primary criteria being met. Thus for example, having the secondary criteria be met in isolation from the primary criteria may not be sufficient for the device to determine that it is outdoors. In particular, the device may only be configured to decide that it is outdoors based on the secondary criteria if the secondary criteria have been met within a predetermined temporally proximal threshold of the primary criteria. Thus, for example, if the secondary criteria occur within some predetermined time of the primary criteria occurring, then the secondary criteria can be used to determine that the device is outdoors. Alternatively or additionally, if the secondary criteria occur within a predetermined number of samples (either samples of the first hardware input sensor related to the primary criteria or samples of the one or more second hardware input sensors related to the secondary criteria) of the primary criteria being met, then the secondary criteria being met can be used in a determination that the device is outdoors. Thus, for example, the primary criteria may be met at a first sample point of the first hardware input sensor. At a second, later sample point, the primary criteria may not be met. In some embodiments, this may cause the system to evaluate the secondary criteria and samples of the one or more second hardware devices. The system may have a threshold time of five samples of the one or more second hardware input sensors. Thus, in this example, while the secondary criteria may not be immediately met, so long as it is met within five samples of the one or more second hardware input sensors, then a determination can be made using the secondary criteria that the device is still outdoors.

The method 600 may be practiced where the one or more secondary criteria include one or more factors related to information collected using an ambient light sensor. Alternatively or additionally, the method 600 may be practiced where the one or more secondary criteria include one or more factors related to information collected using a GPS receiver. Alternatively, or additionally, the method 600 may be practiced where the one or more secondary criteria include one or more factors related to information collected using a barometer. Alternatively or additionally, the method 600 may be practiced where the one or more secondary criteria include one or more factors related to information collected using a microphone.

The method 600 may further include determining that the total amount of time that the device has been outdoors meets a predetermined threshold amount of time and as a result prompting a user with a message based on the predetermined threshold being met. Thus, for example FIGS. 5A and 5B illustrates sample messages that a user may be prompted with when certain amounts of time have expired.

Figure 7:
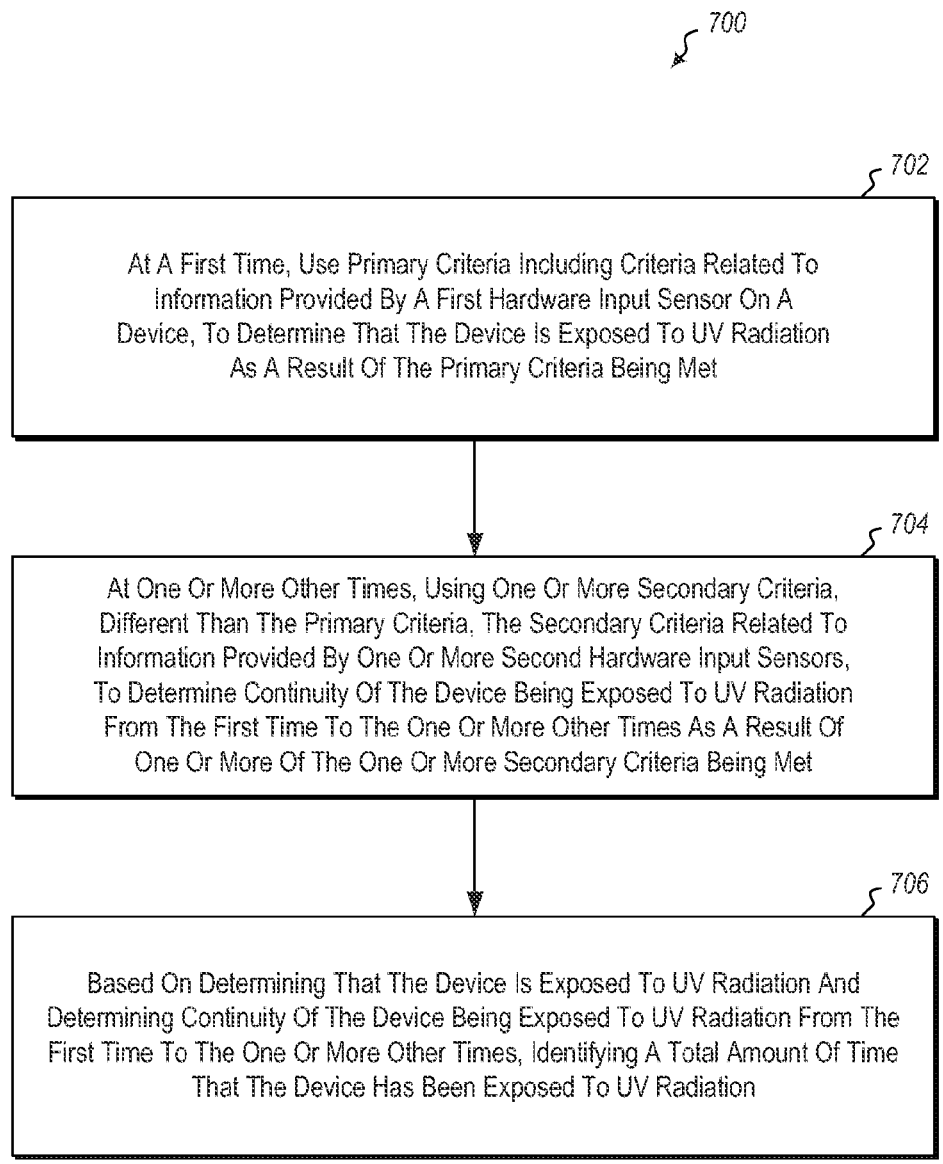
FIG. 7 illustrates a method of determining time spent subject to UV exposure.

Referring now to FIG. 7, a method 700 is illustrated. The method 700 may be practiced in a computing environment and includes acts for determining time spent subject to UV exposure. The method includes at a first time, using primary criteria including criteria related to information provided by a first hardware input sensor on a device, to determine that the device is exposed to UV radiation as a result of the primary criteria being met (act 702). Thus for example, embodiments may have criteria related to UV exposure thresholds. UV exposure may be detected by the UV sensor 102 illustrated in FIG. 1.

The method 700 further includes, at one or more other times (which could be either subsequent or prior times), using one or more secondary criteria, different than the primary criteria, the secondary criteria related to information provided by one or more second hardware input sensors, to determine continuity of the device being exposed to UV radiation from the first time to the one or more other times as a result of one or more of the one or more secondary criteria being met (act 704). Thus, for example, secondary criteria may be related to ambient light, barometric pressure, GPS signals, sound pressure, etc. Other appropriate sensors may be used to detect whether or not these criteria are met. Embodiments can determine that the primary criteria are continuous with the secondary criteria. Thus, in one example, the primary criteria may be met, followed by (or in some embodiments preceded by) the secondary criteria being met without intervening samples (or in some embodiments less than some pre-determine number of samples) where the secondary criteria are not met. Often the primary criteria may be met and then may no longer be met, but the secondary criteria being met may be an indicator that the device remains outdoors.

The method further includes, based on determining that the device is exposed to UV radiation and determining continuity of the device being exposed to UV radiation from the first time to the one or more other times, identifying a total amount of time that the device has been exposed to UV radiation (act 706). Thus, for example, as illustrated above, amount of times exposed to UV radiation can be calculated by subtracting a first time from a most recent time.

The method 700 may further include determining that the primary criteria are no longer met, and be practiced. Where using one or more secondary criteria, different than the primary criteria are performed as a result of determining that the primary criteria are no longer met. Thus, for example, time exposed to UV radiation may be calculated using the primary criteria so long as it is met, but when it is no longer met, embodiments can h evaluate the secondary criteria to see if it is met so as to be able to make a determination that the device is still exposed to UV radiation. In some such embodiments, determining that the primary criteria are no longer met comprises determining that the primary criteria are no longer met over a plurality of samples of information provided by the first hardware input sensor. Thus for example, in some embodiments, the secondary criteria are not evaluated until and unless the primary criteria have not been met for more than some predetermined number of samples from the first hardware input sensors.

The method 700 may be practiced where the one or more secondary criteria are not reliable for indicating that the device is exposed to UV radiation outside of the context of the primary criteria being met. Thus for example, having the secondary criteria be met in isolation from the primary criteria may not be sufficient for the device to determine that is exposed to UV radiation. In particular, the device may only be configured to decide that it is exposed to UV radiation based on the secondary criteria if the secondary criteria have been met within a predetermined temporally proximal threshold of the primary criteria. Thus, for example, if the secondary criteria occur within some predetermined time of the primary criteria occurring, then the secondary criteria can be used to determine that the device is exposed to UV radiation. Alternatively or additionally, if the secondary criteria occur within a predetermined number of samples (either samples of the first hardware input sensor related to the primary criteria or samples of the one or more second hardware input sensors related to the secondary criteria) of the primary criteria being met, then the secondary criteria being met can be used in a determination that the device is exposed to UV radiation. Thus, for example, the primary criteria may be met at a first sample point of the first hardware input sensor. At a second, later sample point, the primary criteria may not be met. In some embodiments, this may cause the system to evaluate the secondary criteria and samples of the one or more second hardware devices. The system may have a threshold time of five samples of the one or more second hardware input sensors. Thus, in this example, while the secondary criteria may not be immediately met, so long as it is met within five samples of the one or more second hardware input sensors, then a determination can be made using the secondary criteria that the device is still exposed to UV radiation.

The method 700 may be practiced where the one or more secondary criteria include one or more factors related to information collected using an ambient light sensor. Alternatively or additionally, the method 700 may be practiced where the one or more secondary criteria include one or more factors related to information collected using a GPS receiver. Alternatively or additionally, the method 700 may be practiced where the one or more secondary criteria include one or more factors related to information collected using a barometer. Alternatively or additionally, the method 700 may be practiced where the one or more secondary criteria include one or more factors related, to information collected using a microphone.

The method 700 may further include determining that the total amount of time that the device has been exposed to UV radiation meets a predetermined threshold amount of time and as a result prompting a user with a message based on the predetermined threshold being met. Thus, for example, FIGS. 5A and 5B illustrates sample messages that a user may be prompted with when certain amounts of time have expired.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

Embodiments of the present invention may comprise or utilize a special purpose or general-purpose computer including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided, over a network or another communications connection (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. In a computing environment, a method of determining time spent outdoors, the method comprising:
   at a first time, determining that the device is outdoors using one or more primary criteria, the one or more primary criteria including information provided by a first hardware input sensor on a device;
   at one or more other times, determining continuity of the device being outdoors from the first time to the one or more other times using one or more secondary criteria, the one or more secondary criteria being both different than the primary criteria and related to information provided by one or more second hardware input sensors, the one or more secondary criteria including a threshold associated with a signal-to-noise ratio, wherein the secondary criteria are used in response to a determination that the one or more primary criteria are no longer being met at a point in time after the first time; and
   based on determining that the device is outdoors and based on determining continuity of the device being outdoors from the first time to the one or more other times, identifying a total amount of time that the device has been outdoors.

2. The method of claim 1, wherein it is determined that the primary criteria are no longer met over a plurality of samples of information provided by the first hardware input sensor.

3. The method of claim 1, wherein the primary criteria comprises criteria related to user input, the user input comprising an indication from a user that the device is currently outdoors.

4. The method of claim 1, wherein the one or more secondary criteria include one or more factors related to information collected using an ambient light sensor.

5. The method of claim 1, wherein the one or more secondary criteria include one or more factors related to information collected using a GPS receiver.

6. The method of claim 1, wherein the one or more secondary criteria include one or more factors related to information collected using a barometer.

7. The method of claim 1, wherein the one or more secondary criteria include one or more factors related to information collected using a microphone.

8. The method of claim 1, further comprising:
   determining that the total amount of time that the device has been outdoors meets a predetermined threshold amount of time; and
   prompting a user with a message based on the predetermined threshold being met.

9. A device configured to detect time spent outdoors, the device comprising:
   one or more first hardware sensors, wherein the one or more first hardware sensors are configured to detect one or more first factors that can be used to determine that a device is outdoors;
   one or more second hardware sensors, wherein the one or more second hardware sensors are configured to detect one or more second factors that can be used to determine that a device is outdoors;
   one or more processors, wherein the one or more processors are configured to:
      at a first time, determine that the device is outdoors using one or more primary criteria, the one or more primary criteria including one or more criteria related to information provided by the one or more first hardware input sensors;
      at one or more other times, determine continuity of the device being outdoors from the first time to the one or more other times using one or more secondary criteria, the one or more secondary criteria being both different than the primary criteria and related to information provided by the one or more second hardware input sensors, the one or more secondary criteria including a threshold associated with a signal-to-noise ratio, wherein the secondary criteria are used in response to a determination that the one or more primary criteria are no longer being met at a point in time after the first time; and
      based on determining that the device is outdoors and determining continuity of the device being outdoors from the first time to the one or more other times, identify a total amount of time that the device has been outdoors.

10. The device of claim 9, wherein it is determined that the primary criteria are no longer met over a plurality of samples.

11. The device of claim 9, wherein the one or more first hardware sensors are configured to detect one or more first factors that can be used to determine that the device is outdoors.

12. The device of claim 9, wherein the one or more second hardware sensors comprise an ambient light sensor.

13. The device of claim 9, wherein the one or more second hardware sensors comprise a GPS receiver.

14. The device of claim 9, wherein the one or more second hardware sensors comprise a barometer.

15. The device of claim 9, wherein the one or more second hardware sensors comprise a microphone.

16. The device of claim 9, further comprising a display, and wherein the one or more processors are configured to:
   determine that the total amount of time that the device has been outdoors meets a predetermined threshold amount of time; and
   prompt a user with a message on the display based on the predetermined threshold being met.

17. A device configured to detect time spent exposed to UV radiation, the device comprising:
   a UV sensor, wherein the UV sensor is configured to detect UV radiation;
   one or more second hardware sensors, wherein the one or more second hardware sensors are configured to detect one or more second factors other than UV radiation that indicate that a device is outdoors, and therefore potentially exposed to UV radiation;
   one or more processors, wherein the one or more processors are configured to:
      at a first time, determine that the device is exposed to UV radiation using one or more primary criteria, the one or more primary criteria including one or more criteria related to UV radiation thresholds;
      at one or more other times, determine continuity of the device being exposed to UV radiation from the first time to the one or more other times using one or more secondary criteria, the one or more secondary criteria being both different than the primary criteria and related to information provided by the one or more second hardware input sensors, the one or more secondary criteria including a threshold associated with a signal-to-noise ratio, wherein the secondary criteria are used in response to a determination that the one or more primary criteria are no longer being met at a point in time after the first time; and
      based on determining that the device is exposed to UV radiation and determining continuity of the device being exposed to UV radiation from the first time to the one or more other times, identify a total amount of time that the device has been outdoors.

18. The device of claim 17, further comprising a display, and wherein the one or more processors are configured to:
   determine that the total amount of time that the device has been exposed to UV radiation meets a predetermined threshold amount of time; and
   prompt a user with a message on the display based on the predetermined threshold being met.

19. The method of claim 9, wherein each measurement associated with the first hardware input sensor and the one or more second hardware input sensors includes a confidence value indicating a confidence level of the device currently being outdoors.

20. The device of claim 17, wherein each measurement associated with the first hardware input sensor and the one or more second hardware input sensors includes a confidence value indicating a confidence level of the device currently being outdoors.

* * * * *